(12) United States Patent
Fujita et al.

(10) Patent No.: US 9,238,612 B2
(45) Date of Patent: Jan. 19, 2016

(54) METHOD FOR PRODUCING UNSATURATED ACID AND/OR UNSATURATED ACID ESTER

(71) Applicant: Asahi Glass Company, Limited, Tokyo (JP)

(72) Inventors: Tomoyuki Fujita, Tokyo (JP); Shinji Wada, Tokyo (JP); Takashi Okazoe, Tokyo (JP); Koichi Murata, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/636,510

(22) Filed: Mar. 3, 2015

(65) Prior Publication Data

US 2015/0175520 A1    Jun. 25, 2015

Related U.S. Application Data

(63) Continuation of application No. PCT/JP2013/073410, filed on Aug. 30, 2013.

(30) Foreign Application Priority Data

Sep. 4, 2012    (JP) .................................. 2012-193801

(51) Int. Cl.
*C07C 67/317*    (2006.01)
*C07C 67/40*    (2006.01)
*C07C 67/00*    (2006.01)
*C07C 51/093*    (2006.01)
*C07C 51/377*    (2006.01)

(52) U.S. Cl.
CPC ............. *C07C 67/317* (2013.01); *C07C 51/093* (2013.01); *C07C 51/377* (2013.01); *C07C 67/00* (2013.01); *C07C 67/40* (2013.01)

(58) Field of Classification Search
CPC .............................. C07C 67/317; C07C 67/40
USPC ......................................................... 560/213
See application file for complete search history.

(56) References Cited

FOREIGN PATENT DOCUMENTS

| JP | S48-064018 A | 9/1973 |
|---|---|---|
| JP | S49-018823 A | 2/1974 |
| JP | H01-213255 A | 8/1989 |
| JP | H06-256250 A | 9/1994 |
| JP | H09-227443 A | 9/1997 |
| JP | 2002-371028 A | 12/2002 |

OTHER PUBLICATIONS

Weizmann et al. Journal of the American Chemical Society, (1948), V. 70, p. 1153-1158 (disclosed in IDS).*
International Search Report dated Dec. 3, 2013 issued in Application No. PCT/JP2013/073410.
Saghatelyan et al., "The reaction of trihalo-tert-butanols with bases in ether and in aqueous and alcoholic media," Khimicheskii Zhurnal Armenii (2000), 53, (1-2), pp. 99-104, Abstract in English, CAN 134, 41908.
Weizmann et al., "The Synthesis of α-Alkoxyisobutyric acids and alkyl methacrylates from acetonechloroform," Journal of the American Chemical Society, Mar. 1948, vol. 70, pp. 1153-1158.

* cited by examiner

*Primary Examiner* — Yong Chu
(74) *Attorney, Agent, or Firm* — Foley & Lardner LLP

(57) ABSTRACT

The present invention relates to a method for producing an unsaturated acid and/or an unsaturated acid ester, containing a process A of reacting a compound (1) represented by the following formula (1) at a temperature of 0° C. to 350° C. in the presence of a Brønsted acid catalyst and/or a Lewis acid catalyst, to prepare a compound (2) represented by the following formula (2);

[Chem. 1]

$$\underset{R^3}{\overset{R^1}{\nearrow}}\!\!\!\underset{CX_3}{\overset{OR^5}{\searrow}}\!\!\!R^4 \qquad (1)$$

[Chem. 2]

$$\underset{R^3}{\overset{R^1}{\nearrow}}\!\!\!\underset{O}{\overset{X}{\searrow}}\!\!\!\underset{OR^6}{\overset{R^4}{\nearrow}} \qquad (2)$$

in which each of $R^1$, $R^2$ and $R^4$ independently represents a hydrogen atom, a deuterium atom or an alkyl group; each of $R^3$ and $R^5$ independently represents a hydrogen atom or a deuterium atom; $R^6$ represents a hydrogen atom, a deuterium atom, or an alkyl group or an aryl group; and X represents a chlorine atom, a fluorine atom, a bromine atom, or an iodine atom.

10 Claims, No Drawings

METHOD FOR PRODUCING UNSATURATED ACID AND/OR UNSATURATED ACID ESTER

CROSS REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2013/073410 filed on Aug. 30, 2013, which is based upon and claims the benefit of priority of Japanese Application No. 2012-193801 filed on Sep. 4, 2012, the entire contents of which are hereby incorporated by reference in their entireties.

TECHNICAL FIELD

The present invention relates to a method for producing an unsaturated acid and/or an unsaturated acid ester, specifically, to a method of producing an unsaturated acid and/or an unsaturated acid ester from a trihaloalcohol in the presence of a specified catalyst.

BACKGROUND ART

As a method for producing an unsaturated acid and/or an ester thereof, such as methacrylic acid (MAA) and/or methyl methacrylate (MMA), the acetone cyanohydrin method (ACH method), which produces methacrylic acid and/or methyl methacrylate from acetone and prussic acid (hydrogen cyanide), has been industrially widely used. However, prussic acid is highly poisonous, and the use thereof is undesirable.

As methods of using no prussic acid, a method of oxidizing isobutene or tertiary butyl alcohol, a method of subjecting propionic acid or propionic acid ester to reaction with formaldehyde or the like, are known. However, any of them have problems when practiced industrially.

A method for producing methacrylic acid or a methacrylic acid ester from a 1,1,1-trihalo-2-methyl-2-propanol is also known. For instance, there is a known method in which 2-methoxy-2-methylpropanoic acid is obtained from 1,1,1-trichloro-2-methyl-2-propanol, then converted into a methyl ester thereof and further dealcoholized, to thereby produce methyl methacrylate (Non-patent Document 1). In producing 2-methoxy-2-methylpropanoic acid, such a method, however, requires to use a basic compound in an amount three times by mole larger than that of the alcohol as a starting material. In addition, in producing methyl methacrylate from methyl 2-methoxy-2-methylpropanoate, one or more equivalent of phosphorous compound or metal chloride is required. Consequently, this method cannot be said to be industrially practicable production method. Further, the chlorine component in the starting material combines with the basic compound to form a salt, and which is difficult to use effectively so long as it remains in a salt form.

As another method for producing methacrylic acid, a method in which 2-chloro-2-methylpropanoic acid is heated up to a temperature of 250° C. to 600° C. in the presence of a catalyst such as calcium chloride is known (Patent Document 1). Further, as a method for producing methyl methacrylate, a method in which methyl 2-chloro-2-methylpropanoate is used as a starting material, heated up to a temperature of 480° C. to 550° C. without catalyst, and then heated up to a temperature of 250° C. to 350° C. in the presence of a dehydrohalogenation catalyst such as a metal chloride is known (Patent Document 2). The 2-chloro-2-methylpropanoic acid and the methyl 2-chloro-2-methylpropanoate can be produced according to, for example, the method for producing 2-bromo-2-methylpropanoic acid through the reaction between 1,1,1-tribromo-2-methyl-2-propanol and potassium hydroxide (Non-patent Document 2). In each of these methods, however, it is required to use the basic compound in an amount two times by mole larger than that of the alcohol as a starting material. Further, the obtained halogen salt is difficult to be used effectively.

CITATION LIST

Patent Literature

Patent Document 1: JP-A-48-64018
Patent Document 2: JP-A-49-18823

Non-Patent Literature

Non-Patent Document 1: Journal of the American Chemical Society, 1948, 70, 1153-1158
Non-Patent Document 2: Khimicheskii Zhumal Armenii (2000), 53, (1-2), 99-104, Abstract in English; CAN 134, 41908

SUMMARY OF THE INVENTION

Problem that the Invention is to Solve

The present invention therefore aims to provide a method capable of producing an unsaturated acid and/or an unsaturated acid ester on an industrial scale without using a large amount of certain chemical such as a basic compound, and further aims to provide a method by which a halogen component can be recovered in a form allowing effective use with ease.

Means for Solving the Problem

The present invention is a method for producing an unsaturated acid and/or an unsaturated acid ester, described in the following [1] to [10].

[1] A method for producing an unsaturated acid and/or an unsaturated acid ester, comprising a process A of reacting a compound (1) represented by the following formula (1) at a temperature of 0° C. to 350° C. in the presence of a Brønsted acid catalyst and/or a Lewis acid catalyst, to prepare a compound (2) represented by the following formula (2).

[Chem. 1]

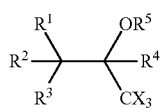

(1)

[Chem. 2]

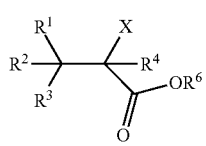

(2)

Here, each of $R^1$, $R^2$ and $R^4$ independently represents a hydrogen atom, a deuterium atom or an alkyl group which has carbon number of 1 to 3 and may be substituted with a halogen atom and/or a deuterium atom; each of $R^3$ and $R^5$ independently represents a hydrogen atom or a deuterium atom; $R^6$ represents a hydrogen atom, a deuterium atom, or an alkyl group or an aryl group which has carbon number of 1 to 8 and may be substituted with a halogen atom and/or a deuterium atom; and X represents a chlorine atom, a fluorine atom, a bromine atom, or an iodine atom.

[2] The production method according to the above [1], in which the Brønsted acid catalyst and/or the Lewis acid catalyst is a compound represented by the following general formula (A) or mixture thereof;

$$M_n Y_m \qquad (A)$$

Here, M represents a hydrogen ion or a cation of metal or metalloid selected from the group consisting of the group 2 elements and the group 4-14 elements in the periodic table; Y represents an anion selected from the group consisting of halide ions, a sulfate ion, a nitrate ion, a carbonate ion, a hydrogencarbonate ion, a sulfide ion, an oxide ion, a hydroxide ion, an alkoxide ions, a phosphate ion, an acetate ion, and a perchlorate ion; and n and m are numbers satisfying the expression, cation M's valence×n=anion Y's valence×m.

[3] The production method according to the above [2], in which M is a cation of metal selected from the group consisting of zinc, iron and copper, and Y is a fluoride ion, a chloride ion or a bromide ion.

[4] The production method according to the above [1], in which the Lewis acid catalyst is an activated clay, an acid clay, a zeolite, a heteropoly acid, or an ion exchange resin.

[5] The production method according to any one of the above [1] to [4], in which the Brønsted acid catalyst and/or the Lewis acid catalyst is present in a ratio of 0.001 to 1 mol with respect to 1 mol of the compound (1).

[6] The production method according to any one of the above [1] to [5], in which the process A contains a step of adding an alcohol which has carbon number of 1 to 8 and may be substituted with a halogen atom and/or a deuterium atom, exclusive of the compound (1) represented by formula (1), and/or water.

[7] The production method according to any one of the above [1] to [6], further comprising, subsequent to the process A, a process B of preparing a compound (3) represented by the following formula (3) from the product of the process A containing the compound (2);

[Chem. 3]

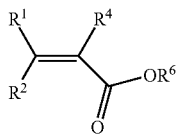
(3)

Here, $R^1$, $R^2$, $R^4$ and $R^6$ have the same meanings as above, respectively.

[8] The production method according to any one of the above [1] to [7], in which each of $R^1$, $R^2$, $R^4$ and $R^6$ is independently a hydrogen atom, a deuterium atom, or an alkyl group which has carbon number of 1 to 3 and may be substituted with a deuterium atom.

[9] The production method according to the above [8], in which each of $R^1$ and $R^2$ is independently a hydrogen atom or a deuterium atom, and each of $R^4$ and $R^6$ is a methyl group which may be substituted with a deuterium atom.

[10] The production method according to the above [9], further comprising, prior to the process A, a process C of reacting an acetone which may be substituted with a deuterium atom, with a halogenoform or a deuterated halogenoform, to prepare the compound (1).

Advantageous Effect of the Invention

According to the method of the present invention, an unsaturated acid and/or an unsaturated acid ester can be produced on an industrial scale in the presence of a small amount of reusable catalyst. Further, a halogen component can be recovered in the form of a halogen acid which is easy to use effectively.

MODE FOR CARRYING OUT THE INVENTION

The method of the present invention contains a process A of reacting a compound (1) represented by the following formula (1) at a temperature of 0° C. to 350° C. in the presence of a Brønsted acid catalyst and/or a Lewis acid catalyst, to prepare a compound (2) represented by the following formula (2).

[Chem. 4]

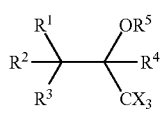
(1)

[Chem. 5]

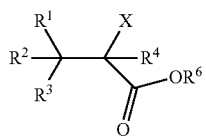
(2)

In formulae (1) and (2), each of $R^1$, $R^2$ and $R^4$ independently represents a hydrogen atom, a deuterium atom or an alkyl group which has carbon number of 1 to 3 and may be substituted with a halogen atom and/or a deuterium atom. The alkyl group includes a methyl group, an ethyl group, a propyl group, and a group where at least one hydrogen atom of these groups is substituted by a halogen atom and/or a deuterium atom. It is preferable that each of $R^1$, $R^2$ and $R^4$ be independently a hydrogen atom, a deuterium atom or an alkyl group which has carbon number of 1 to 3 and may be substituted with a deuterium atom. $R^3$ represents a hydrogen atom or a deuterium atom. It is more preferable that each of $R^1$ to $R^3$ be independently a hydrogen atom or a deuterium atom and $R^4$ be a methyl group any of whose hydrogen atoms may be deuterium atom(s).

In formula (1), $R^5$ represents a hydrogen atom or a deuterium atom. In formula (2), $R^6$ represents a hydrogen atom, a deuterium atom, or an alkyl group or an aryl group which has carbon number of 1 to 8 and may be substituted with a halogen atom and/or a deuterium atom. Examples of $R^6$ include a butyl group, a pentyl group, a hexyl group, a heptyl group, an octyl group, a phenyl group, a benzyl group, a tolyl group, and a group where at least one hydrogen atom of these groups is substituted by a halogen atom and/or a deuterium atom, in addition to those recited as $R^1$ to $R^4$. $R^6$ is preferably a hydrogen atom, a deuterium atom or an alkyl group which has carbon number of 1 to 3 and may be substituted with a deuterium atom and more preferably a methyl group substituted with a deuterium atom.

In formulae (1) and (2), X represents a fluorine atom, a chlorine atom, a bromine atom or an iodine atom, and is preferably a chlorine atom or a bromine atom.

Incidentally, the compound (1) may take the form of a hydrate thereof, or a methanol, ethanol or other alcohol adduct thereof.

As the Brønsted acid catalyst and/or the Lewis acid catalyst, the compound represented by the following general formula (A) or mixture thereof is preferable.

$$M_n Y_m \quad (A)$$

Here, M represents a hydrogen ion or a cation of metal or metalloid selected from the group consisting of the group 2 elements and the group 4-14 elements in the periodic table; Y represents an anion selected from the group consisting of halide ions, a sulfate ion, a nitrate ion, a carbonate ion, a hydrogencarbonate ion, a sulfide ion, an oxide ion, a hydroxide ion, an alkoxide ions, a phosphate ion, an acetate ion, and a perchlorate ion; and n and m are numbers satisfying the expression, cation M's valence x n=anion Y's valence×m.

The M is more preferably a hydrogen ion, a boron ion, or a cation of metal selected from the group consisting of magnesium, aluminum, calcium, titanium, vanadium, chromium, manganese, iron, cobalt, nickel, copper, zinc, gallium, germanium, strontium, zirconium, niobium, molybdenum, ruthenium, rhodium, palladium, silver, cadmium, indium, tin, antimony, barium, hafnium, tantalum, tungsten, rhenium, osmium, iridium, platinum, gold, mercury, thallium, and lead, and particularly preferably a cation of metal selected from the group consisting of iron, zinc and copper.

Y is preferably a halide ion, an oxide ion or a sulfide ion, and particularly preferably a fluoride ion, a chloride ion or a bromide ion.

Specific examples of the $M_n Y_m$ include boron trichloride, iron chloride, copper chloride, zinc chloride, tin chloride, lead chloride, boron trifluoride, iron fluoride, copper fluoride, zinc fluoride, tin fluoride, lead fluoride, iron bromide, copper bromide, zinc bromide, tin bromide, lead bromide, iron oxide, copper oxide, zinc oxide, tin oxide, lead oxide, iron sulfide, copper sulfide, zinc sulfide, tin sulfide, and lead sulfide.

In addition to them, a solid acid can be used as the Lewis acid catalyst. The solid acid includes activated clay, acid clay, zeolite, heteropoly acids, and ion exchange resins.

The activated clay is a compound prepared by treating naturally occurring acid clay (montmorillonite-type clay) with a mineral acid such as sulfuric acid, and has a porous structure. Typical chemical constituents they have in common are $SiO_2$, $Al_2O_3$, $Fe_2O_3$, CaO, MgO and so on.

The heteropoly acid is a composite oxide acid which is generally constituted of two or more different kinds of oxide complexes, or one where protons of them are replaced in part or in entirety with other cations. The heteropoly acid is, for example, constituted of an oxoacid ion of such element as phosphorus, arsenic, tin, silicon, titanium, or zirconium (e.g. phosphoric acid, silicic acid) and an oxoacid ion of such element as molybdenum, tungsten, vanadium, niobium, or tantalum (e.g. vanadic acid, molybdic acid, tungstic acid), and a wide variety of heteropoly acids can be formed by variously combining them.

Elements of oxoacids forming a heteropoly acid are not particularly limited, and examples thereof include copper, beryllium, boron, aluminum, carbon, silicon, germanium, tin, titanium, zirconium, cerium, thorium, nitrogen, phosphorus, arsenic, antimony, vanadium, niobium, tantalum, chromium, molybdenum, tungsten, uranium, selenium, tellurium, manganese, iodine, iron, cobalt, nickel, rhodium, osmium, iridium, and platinum.

In carrying out the reaction in a batch system, the amount of such catalyst is preferably 0.001 mol to 1 mol, more preferably 0.03 mol to 0.3 mol, and most preferably 0.04 mol to 0.25 mol, with respect to 1 mol of compound (1). If the used amount is less than the lower limit specified above, it is inappropriate from the viewpoint of productivity, and if it exceeds 1 mol, it is also inappropriate from the viewpoint of volumetric efficiency.

The catalyst can be used in a state of being supported on a carrier as required. The carrier has no particular restriction on the kind thereof, and an oxide of metal or metalloid, a salt thereof, inorganic carbon or the like can be used, with examples including silica, alumina, titania, zirconia, zeolite, and activated carbon.

In addition, it is preferred that at least a portion of the catalyst be reused. When the catalyst suffers deactivation, it is preferred that a portion or all thereof is retreated and used. As a retreatment method, a method of heating in an inert gas atmosphere or an oxygen-containing gas atmosphere, a method of treating the catalyst with a hydrogen halide gas or an aqueous solution of hydrogen halide, and combinations thereof can be mentioned.

The reaction temperature can be adjusted as appropriate according to compound (1) and catalyst, but typically it is preferably from 0° C. to 350° C., more preferably from 50° C. to 300° C., and particularly preferably from 50° C. to 250° C. If the temperature is too low, it is inappropriate from the viewpoint of productivity, and if the temperature is too high, it is also inappropriate because it causes decomposition of the starting material or the product and because it causes the increase in side reaction.

It is preferable that the reaction pressure is adjusted as appropriate according to the vapor pressures of compound (1), solvent and other gases and the like, and it may be performed under an applied pressure or under a reduced pressure. It is, as expressed in absolute pressure, preferably from 0 MPa to 10 MPa, more preferably from 0.05 MPa to 2 MPa, and most preferably from 0.1 MPa to 1 MPa.

As to a mode of the reaction, it may be carried out in either a liquid phase or a vapor phase, and it may be performed in either a batch system or a continuous system. In every case, a compound or a gas which reacts chemically with neither the starting material nor the reaction product can be used as a solvent or a diluent gas, respectively, from the viewpoint of handling of the starting material and control of reaction heat. Examples of such a solvent include pentane, hexane, heptane, petroleum ether, dimethyl ether, diethyl ether, tetrahydrofuran, 1,2-dimethoxyethane, dichloromethane, chloroform, carbon tetrachloride, dichloroethane, acetic acid, benzoic acid, acetic anhydride, ethyl acetate, acetone, 2-butanone, acetonitrile, dimethylformamide, dimethylacetamide, dimethyl sulfoxide, benzene, toluene, chlorobenzene, dichlorobenzene, benzonitrile, nitromethane, nitrobenzene, and mixtures thereof. As the diluent gas, a nitrogen gas, a helium gas, an argon gas, and mixtures thereof, can be mentioned.

The amount of the solvent or the diluent gas used is preferably within the range that the concentration of compound (1) becomes 5 wt % or higher, and more preferably 10 wt % or higher. If the concentration of compound (1) is too low, it is inappropriate from the viewpoint of productivity.

The process A preferably contains a step of adding an alcohol which has carbon number of 1 to 8 and may be substituted with a halogen atom and/or a deuterium atom (from which the compound (1) represented by the above-mentioned formula (1) is excluded) and/or water (hereinafter referred to as "an alcohol and the like"). This addition may be conducted at any point in time, and an alcohol and the like may be present from the beginning of the process A. By allowing them to be present during the reaction, it becomes feasible to produce esters or carboxylic acids of the compound (2) efficiency in the same reactor or at a reduction in the time required for continuing reaction.

Specific examples of such an alcohol include methanol, ethanol, butanol, isobutyl alcohol, tertiary butyl alcohol, pentanol, hexanol, cyclohexanol, heptanol, 2-ethylhexanol, phenol, benzyl alcohol, and one where at least a part of hydrogen atoms of these molecules is substituted by a halogen atom and/or a deuterium atom.

Specific examples of a halogen-substituted alcohol include 2,2,2-trichloroethanol, 2,2,3,3-tetrafluoropropanol, 1,1,1,3,3,3-hexafluoro-2-propanol, and fluoroalkylalcohols represented by the general formula $C_nF_{2n+1}(CH_2)_mOH$ (in which n is an integer of 1 to 8 and m is an integer of 1 to 3). Specific examples of $C_nF_{2n+1}(CH_2)_mOH$ include $CF_3CH_2OH$, $CF_3CF_2CH_2OH$, $CF_3CF_2CF_2CH_2OH$, $CF_3CF_2CH_2CH_2OH$, $CF_3(CF_2)_3CH_2CH_2OH$, $CF_3(CF_2)_5CH_2CH_2OH$, $CF_3(CF_2)_7CH_2CH_2OH$, $CF_3CF_2(CH_2)_3OH$, $CF_3(CF_2)_3(CH_2)_3OH$, and $CF_3(CF_2)_5(CH_2)_3OH$.

Specific examples of a deuterium-substituted alcohol include methanol and ethanol at least a part of whose hydrogen atoms is substituted by a deuterium atom.

Methanol, ethanol, and/or one where at least a part of hydrogen atoms thereof is substituted by a halogen atom and/or a deuterium atom are preferably used, and methanol is most preferable.

The addition amount of the alcohol and the like is preferably 0.5 to 20 mol, more preferably 1 to 10 mol, and particularly preferably 1 to 5 mol, with respect to 1 mol of compound (1). If the addition amount of the alcohol and the like is less than the lower limit specified above, there are cases where a sufficiently high conversion rate cannot be attained. On the other hand, if the addition amount of the alcohol and the like exceeds the upper limit specified above, the volumetric efficiency is reduced and productivity is lowered. Additionally, it doesn't matter that the alcohol and the like are used simultaneously with the solvent or the diluents gas as recited above.

The turnaround time of the process A varies depending on the catalyst, the temperature and so on, and, when the reaction is carried out in a batch system, it is preferably from 10 minutes to 12 hours. It is preferable to conduct the process A while monitoring the progress of the reaction with detecting the generation of the compound (2) by gas chromatography or the like.

In the case of a continuous reaction system, the space velocity therein is preferably from 1 to 500,000 $h^{-1}$, more preferably from 100 to 50,000 $h^{-1}$, and most preferably from 100 to 10,000 $h^{-1}$. The term space velocity as used herein refers to the weight space velocity per catalyst weight, and to the value obtained by dividing a flow rate (kg/h) of compound (1) by the weight (kg) of a catalyst including a carrier and the like. Additionally, the reciprocal of the space velocity is referred to as a contact time or a residence time.

In the process A, in addition to the compound (2), the following compound (3) can be produced. That is, the product obtained in the process A may be a mixture containing the compound (2) and the compound (3). Accordingly, an intended compound (3) can be obtained in one step of the process A, however, it is preferable to carry out the following process B.

That is, the method of the present invention preferably contains a process B of preparing an unsaturated compound (3) represented by the following formula (3) from the product in the process A containing a compound (2).

[Chem. 6]

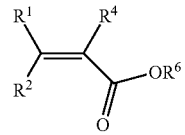

(3)

In formula (3), $R^1$, $R^2$, $R^4$ and $R^6$ have the same meanings as in the definitions of compounds (1) and (2), respectively.

The process B can be performed through an equivalence reaction between a compound (2) and various basic compounds, in a catalytic reaction process or under irradiation with light, ultrasonic waves or microwaves. As to the basic compounds, metal hydroxides, metal oxides, metal carbonates, metal alkoxides, metal amides, and amines are preferable in viewpoint of availability, and metal hydroxides, metal oxides, metal carbonates, metal alkoxides, and amines are more preferable. From the economical point of view, metals in these compounds are preferably lithium, sodium, potassium, calcium, and magnesium, and more preferably sodium, potassium and calcium.

As an alcohol forming a metal alkoxide, a linear or branched alcohol which has carbon number of 1 to 8 and may have a halogen atom, or a phenol is preferable, and a linear or branched alcohol having carbon number of 1 to 4 is more preferable. The metal alkoxide used is converted into an alcohol and a metal halide by the reaction with a compound (2). Since the alcohol can recover to a metal alkoxide through the reaction with a metal hydroxide, a metal oxide or a metal carbonate, or the like, it can be reused.

Examples of the basic compounds include sodium hydroxide, potassium hydroxide, calcium hydroxide, calcium oxide, calcium carbonate, sodium methoxide, potassium methoxide, sodium ethoxide, potassium ethoxide, sodium propoxide, potassium propoxide, sodium butoxide, potassium butoxide, sodium tertiary butoxide, and potassium tertiary butoxide.

As the amines, tertiary amines are preferred, and triethylamine, trimethylamine, diisopropylethylamine, pyridine, tetramethylethylenediamine, diazabicycloundecene, diazabicyclononene, and basic ion exchange resins are more preferred. These amines are converted into, for example, salts of hydrogen halides by the reaction with a compound (2). Since the salts can be converted into amines and metal halides by the reaction with metal hydroxides, metal oxides, metal carbonates, and/or aqueous solutions thereof, it can be reused.

As to a mode of the reaction, it may be carried out in either a liquid phase or a vapor phase, and it may be performed in either a batch system or a continuous system. In either of the liquid-phase and vapor-phase cases, various compounds or gases can be used as solvents or diluent gases, respectively, from the viewpoints of handling of the starting material and control of reaction heat. As for the solvents and the diluent gases, those described for the process A can be used. In addition, if the solvent, water or alcohols used in the process A still remains, it can be utilized as a solvent or a diluent gas.

The reaction temperature can be varied depending on the catalyst used or the like, and, it is preferably from 0° C. to 600° C., and more preferably from 150° C. to 550° C. If the temperature is too low, it is inappropriate from the viewpoint of productivity, and if the temperature is too high, it is also inappropriate because it causes decomposition of the starting material or the product and because it causes the increase in side reaction.

It is preferable that the reaction pressure is adjusted as appropriate according to the vapor pressures of compound (2), solvent and other gases and the like, and it may be performed under an applied pressure or under a reduced pressure. It is, as expressed in absolute pressure, preferably from 0 MPa to 10 MPa, more preferably from 0.05 MPa to 2 MPa, and most preferably from 0.1 MPa to 1 MPa.

The process B may be carried out in a reactor different from that used for the process A or in the same reactor as used for the process A. However, when each of $R^1$ to $R^3$ in the compound (2) is a hydrogen atom or a deuterium atom, HX or DX is produced simultaneously with the compound (3) in the process B. It is therefore appropriate that the reactor for the process B be resistant to them. For example, a reactor made of mild steel, stainless steel, nickel, Inconel, hastelloy, or glass, or a reactor lined with a fluororesin can be used.

HX and DX can be used for various purposes. For example, they serve as raw materials of vinyl halides, halogenated methanes, other halogenated alkanes, halogenated aryls, halogen gases, or metal halides. The thus obtained halogenated methane and halogen gas can serve as raw materials of trihalomethane, which is a starting material of a compound (1).

The method of the present invention preferably contains a process for preparing the compound (1) prior to the process A. Examples of the preparation method include the method of reacting a ketone or an aldehyde with a trihalomethane in the copresence of a basic compound (JP-A-49-82611, U.S. Pat. No. 2,462,389, Journal of Organic Chemistry, 2000, 65, 7211-7212), the method of electrochemically reacting a ketone with carbon tetrachloride (Tetrahedron Letters, 1986, 27(27), 3129-32), and the method of reacting a trihaloacetaldehyde or a trihaloacetone with an aromatic compound (J. Org. Chem., 2000, 65, 1597-1599, Japanese Patent 3,883, 354).

When each of $R^1$ to $R^3$ in the compound (1) is independently a hydrogen atom or a deuterium atom and each of $R^4$ and $R^6$ is a methyl group which may be substituted with a deuterium atom, the method of the present invention preferably contains a process C of reacting an acetone which may be substituted with a deuterium atom, with a halogenoform or a deuterated halogenoform, to prepare the compound (1). Deuterated halogenoforms, notably deuterochloroform, are readily available as compared with deuterium cyanide, and they are suitable as raw materials of deuterated unsaturated acid esters. Polymers derived from deuterated MMAs can be utilized as optical fibers usable in high-capacity high-speed transmission systems and the like.

In addition, the method of the present invention preferably contains a process for purifying the compound (3) obtained in the process B. As the purification method, distillation, sublimation, crystallization, washing with a liquid, filtration, and combinations thereof can be mentioned, and it is preferred to perform a purification containing at least a crystallization or distillation step, and more preferred to perform a purification containing a distillation step.

The distillation can be carried out according to a known method. The distillation column used may be a commonly-used distillation column, such as a distillation column containing sieve trays, dual trays, bubble cap trays, Sulzer packing, TECHNOPACK packing, Mellapack packing, Raschig-ring packing, Pall-ring packing, or CASCADE MINI-RINGS packing. In addition, some of these distillation systems can be combined as appropriate and made available for use.

In distillation, a polymerization inhibitor may be added as appropriate. As the polymerization inhibitor, hydroquinone (HQ), monomethyl ether of hydroquinone (MEHQ), phenothiazine (PTZ), a hindered amine radical scavenger compound, or a catechol such as t-butyl catechol or di-t-butylcatechol can be mentioned. In addition, the presence of an oxygen-containing gas is also effective in inhibiting polymerization. Further, it is known that copper-containing metallic compounds can inhibit polymerization. For the purpose of preventing unintended polymerization from occurring in the case of adding no polymerization inhibitor, it is appropriate to choose a distillation column of the type which has a small residence section.

The temperature and pressure conditions during the distillation operation may be the same ones as adopted usually in the case of distilling unsaturated acids or esters thereof. For example, a temperature lower than 80° C. is selected for the purpose of minimizing polymerization at the bottom of the column, and the determination of vapor pressure is based on the temperature setting.

Further, for the purpose of eliminating impurities, treatment by using various amines or other compounds, or with activated carbon, alumina or a resin-made adsorbent may be carried out. Crystallization is also an effective method for impurity reduction.

Filtration is effective at eliminating trace amounts of polymers produced unintentionally during operations such as reaction and distillation. The filtration can be performed by means of a strainer, a filter, a centrifugal filter, or the like.

Further, if the compound (3) is methyl methacrylate, there is a case where it is obtained in a state of a mixture with methanol, and it is known that these two compounds form an azeotropic mixture. For such a case, a method for collecting each of methyl methacrylate and methanol by carrying out distillation using azeotropic solvent or by a separation process using layer separation is known (JP-A-11-124347).

By undergoing these purification steps, the compound (3) becomes easy to subject to polymerization reaction, and allows production of a colorless polymeric material having excellent heat resistance and transparency.

It goes without saying that the method of the present invention may contain condensation, distillation, sublimation, crystallization, washing with a liquid, filtration, or other purification steps between the respective processes.

Further, the thus obtained compound (2) or compound (3) can be converted into other esters or carboxylic acids in accordance with known methods. As such a method, there is a method of heating the compound (2) or (3) together with water and/or alcohols in the presence of a catalytic amount of acid or base.

EXAMPLES

The present invention will be illustrated in detail by reference to the following examples and comparative examples, but the present invention should not be construed as being limited to these examples.

Incidentally, in the following, gas chromatography is abbreviated to GC and GC mass spectrometry is abbreviated to GC-MS. The term yield refers to the isolated yield unless otherwise indicated. The yield determined from an area ratio between peaks of an NMR spectrum is defined as an NMR yield. In addition, the purity determined from an area ratio between peaks in GC is defined as GC purity. The pressure refers to gage pressure unless otherwise indicated. Reactions concerned with compounds sensitive to oxygen or moisture were carried out in a stream of nitrogen.

Example 1

Into a 100-mL three necked flask were added 36.7 g (0.63 mol) of acetone and 15.0 g (0.13 mol) of chloroform, followed by cooling to −10° C. Thereto was added 3.0 g (0.008 mol) of a 50 wt % aqueous sodium hydroxide solution having prepared separately, followed by stirring for 20 minutes. Then the temperature was gradually raised to room temperature. A portion of the crude reaction solution obtained was sampled, mixed with dichloromethane as an internal standard, and analyzed by means of gas chromatography. As a result of the analysis, the conversion of chloroform was 49% and the selectivity for 1,1,1-trichloro-2-methyl-2-propanol with respect to chloroform was 92%.

Example 2

Into a 50-mL three necked flask equipped with a Dimroth condenser were added 15.14 g (0.080 mol) of 1,1,1-trichloro-2-methyl-2-propanol hemihydrate (hereafter referred to as "starting material alcohol" in some cases) and 2.00 g (0.016 mol, or 0.2 mol per mol of the starting material alcohol) of zinc chloride, followed by heating with stirring until the inside temperature was raised to 125° C., and kept for 30 minutes in such a state. After cooling the reactor, a portion of the crude reaction solution obtained was sampled, mixed with dichloromethane as an internal standard, and analyzed by means of gas chromatography.

As a result of the analysis, it was found out that, as mentioned below, the conversion of 1,1,1-trichloro-2-methyl-2-propanol was 85.4% and the yield of 2-chloro-2-methylpropanoic acid was 54.4%. As to other products, it was obtained methacrylic acid in a 2.3% yield, (1,1,1-trichloro-2-methyl-2-propyl) methacrylate in a 22.7% yield, and (1,1,1-trichloro-2-methyl-2-propyl) 2-chloro-2-methylpropanoate in a 7.8% yield.

[Chem. 7]

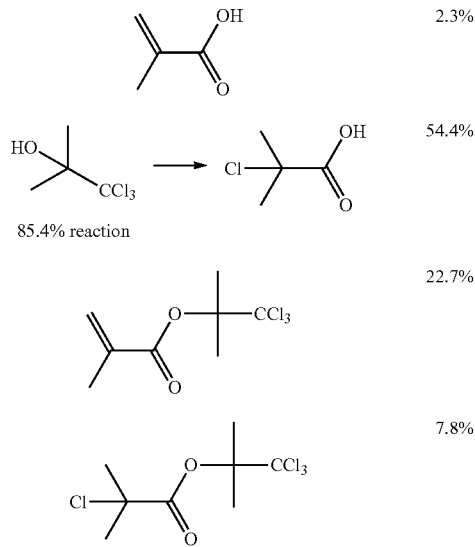

Example 3

A nitrobenzene solution containing 12.1 wt % of 1,1,1-trichloro-2-methyl-2-propanol was prepared by mixing 30.55 g of 1,1,1-trichloro-2-methyl-2-propanol hemihydrate and 213.31 g of nitrobenzene and drying by Molecular Sieves 4A. Reaction was performed in the same manner as in Example 2, except that 30.80 g of the solution (containing 3.7 g (0.021 mol) of 1,1,1-trichloro-2-methyl-2-propanol) and 0.14 g (0.001 mol, or 0.05 mol with respect to the starting material alcohol) of zinc chloride were used, the reaction temperature was 105° C., the reaction time was set at 14 hours and nitrogen gas was supplied into the reactor at 100 ml/min. The gas emitted from the reactor was absorbed into an aqueous sodium hydroxide solution, and then titration was performed. As a result, it was found out that 0.021 mol of hydrogen chloride was produced.

To 2.83 g of the crude reaction solution obtained was added 0.11 g of methanol, followed by heating at 60° C. for 4 hours. Then, it was found out by gas chromatography analysis that the conversion of the 1,1,1-trichloro-2-methyl-2-propanol was 86.0% and the yield of methyl 2-chloro-2-methylpropanoate was 10.2%. As to other products, it was obtained methyl methacrylate in a 0.2% yield, methacrylic acid in a 8.7% yield, (1,1,1-trichloro-2-methyl-2-propyl) methacrylate in a 13.1% yield, and (1,1,1-trichloro-2-methyl-2-propyl) 2-chloro-2-methylpropanoate in a 22.8% yield.

Example 4

A nitrobenzene solution of 12.3 wt % 1,1,1-trichloro-2-methyl-2-propanol was prepared in the same manner as in Example 3. In a 50-mL three necked flask equipped with a Dimroth condenser, 40.68 g of the nitrobenzene solution of 1,1,1-trichloro-2-methyl-2-propanol (containing 5.0 g (0.029 mol) of 1,1,1-trichloro-2-methyl-2-propanol), 0.18 g (0.001 mol, or 0.03 mol with respect to 1 mol of the starting material alcohol) of zinc chloride and 1.28 g of methanol were mixed, and allowed to react for one hour at 115° C., and additional one hour at 130° C. Thereto was further added 3.00 g of methanol, and allowed to react at 85° C. for 10 minutes. Thereafter, analysis was performed by means of gas chromatography.

The analysis of the crude reaction solution by gas chromatography revealed that the conversion of 1,1,1-trichloro-2-methyl-2-propanol was 70.0% and the yield of methyl 2-chloro-2-methylpropanoate was 23.9%. As to other products, it was obtained methyl methacrylate in a 0.7% yield, methacrylic acid in a 0.2% yield, (1,1,1-trichloro-2-methyl-2-propyl) methacrylate in a 7.8% yield, and (1,1,1-trichloro-2-methyl-2-propyl) 2-chloro-2-methylpropanoate in a 12.9% yield.

Example 5

A nitrobenzene solution of 12.1 wt % 1,1,1-trichloro-2-methyl-2-propanol was prepared in the same manner as in Example 3. Reaction was performed in the same manner as in Example 2, except that 999.92 g of the solution (120 g (0.68 mol) of 1,1,1-trichloro-2-methyl-2-propanol) and 99.51 g (0.68 mol, or 1 mol with respect to 1 mol of the starting material alcohol) of zinc chloride were used and the reaction time was set at 6 hours. The gas emitted from the reactor was absorbed into an aqueous sodium hydroxide solution, and then titration was performed. As a result, it was found out that 0.638 mol of hydrogen chloride was produced. The crude reaction solution obtained was filtered with suction filtration, mixed with 37.37 g of methanol, and then heated at 60° C. for 5 hours.

An analysis of the crude reaction solution by gas chromatography revealed that the conversion of 1,1,1-trichloro-2-methyl-2-propanol was 67.7% and the yield of methyl 2-chloro-2-methylpropanoate was 36.5%. As to other products, it was obtained (1,1,1-trichloro-2-methyl-2-propyl) methacrylate in a 10.5% yield, and (1,1,1-trichloro-2-methyl-2-propyl) 2-chloro-2-methylpropanoate in a 13.5% yield. The crude reaction solution obtained was distilled under a reduced pressure, thereby obtaining methyl 2-chloro-2-methylpropanoate at a purity of 85%.

Example 6

Into a 10-ml of recovery flask equipped with a Dimroth condenser were added 1.01 g of the methyl 2-chloro-2-methylpropanoate obtained in Example 4, 1.421 g of sodium methoxide as a base (a 28 wt % methanol solution) and 0.096 g of THF as an internal standard, and allowed to react at 70° C. for 2 hours.

An analysis of the obtained crude reaction solution by gas chromatography revealed that the conversion of methyl 2-chloro-2-methylpropanoate was 68.8% and the yield of methyl methacrylate was 13.6%. As to another product, methyl 3-methoxy-2-methylpropanoate was obtained in an 18.0% yield.

Example 7

Into a 3-liter three necked flask were charged 502.8 g (2.696 mol) of 1,1,1-trichloro-2-methyl-2-propanol hemihydrate and 1,507 g (15.23 mol) of 1,2-dichloroethane. A distillation column was attached thereto, an azeotropic mixture of 1,2-dichloroethane and water was distilled away, and the rest was further concentrated. The distillation column was replaced with a reflux condenser, and thereto was added dropwise 551.6 g (5.624 mol) of sulfuric acid over 40 minutes while the inside temperature was kept at 35° C. or lower. After the completion of dropwise addition, intense generation of hydrochloric acid gas was confirmed. The stirring was carried out all night as it stood.

Thereto was further added 259.7 g (8.111 mol) of methanol over 60 minutes, heated up to 60° C., and stirred for 6 hours.

The reflux condenser was replaced with a distillation column, the pressure of the system was reduced to 5.3 kPa and fractions having boiling points up to 52° C. were distilled away, to thereby obtain 401.0 g of a crude solution. The crude solution was distilled by using a packed tower, whereby 306.8 g (2,246 mol, boiling point: 133-134° C., yield: 83%) of the mentioned compound (methyl 2-chloro-2-methylpropanoate) was obtained at a GC purity of 99% or higher.

$^1$H-NMR (300.4 MHz, CDCl$_3$, TMS) δ; 1.79 (s, 6H), 3.80 (s, 3H).

Example 8

Into a 200-ml three necked flask were added 12.7 g (68.3 mmol) of 1,1,1-trichloro-2-methyl-2-propanol hemihydrate and 48.6 g (491 mmol) of 1,2-dichloroethane. A distillation column was attached thereto, an azeotropic mixture of 1,2-dichloroethane and water was distilled away, and the rest was further concentrated. The distillation column was replaced with a reflux condenser, and thereto was added 2.00 g (20.4 mmol) of sulfuric acid. The stirring was performed at 90° C. for 14 hours as it stood.

It was cooled to room temperature, and thereto was added 6.60 g (200 mmol) of methanol, heated up to 60° C., and stirred for 5.5 hours.

The contents were poured into 80 g of water, and extracted once with 40 mL of dichloromethane and three times with 20 mL. The organic layer was washed twice with 20 mL of brine, dried over magnesium sulfate, and then concentrated, thereby obtaining 13.7 g of a crude solution. An NMR analysis revealed that the crude solution contained 6.69 g (49.0 mmol) of methyl 2-chloro-2-methylpropanoate. The NMR yield was 72%.

Example 9

Into a 100-ml three necked flask was added 12.7 g (68.0 mmol) of 1,1,1-trichloro-2-methyl-2-propanol hemihydrate, a distillation column was attached thereto, and thereto was added 13.5 g (136 mmol) of sulfuric acid. The stirring was performed at room temperature for 7 hours as it stood, and thereto was further added 13.4 g (135 mmol) of sulfuric acid, followed by stirring for 16 hours at room temperature.

Thereto was further added 10.9 g (340 mmol) of methanol, heated up to 60° C., and stirred for 6 hours.

The contents were poured into 100 g of ice water, and extracted once with 40 mL of dichloromethane and three times with 20 mL. The organic layer was washed twice with 20 mL of brine, dried over magnesium sulfate, and then concentrated, thereby obtaining 12.2 g of a crude solution. An NMR analysis revealed that the crude solution contained 8.76 g (64.2 mmol) of methyl 2-chloro-2-methylpropanoate. The NMR yield was 94%.

Example 10

A 1,2-dichloroethane solution containing 28 wt % of 1,1,1-trichloro-2-methyl-2-propanol was prepared by mixing 1,1,1-trichloro-2-methyl-2-propanol hemihydrate and 1,2-dichloroethane and drying by Molecular Sieves 4A. In a three necked flask an exit of which was connected to a Dimroth condenser, 10 g of the solution (containing 2.89 g (0.016 mol) of 1,1,1-trichloro-2-methyl-2-propanol), 20 g of 1,2-dichloroethane and 4.26 g of activated clay (F-24X, a product of N.E. CHEMCAT CORPORATION) were mixed in a stream of nitrogen, heated at 50° C. for 2 hours, and then heated at 95° C. under reflux for 8 hours. Thereto was added dropwise 1.56 g (0.049 mol) of methanol by means of a dropping funnel, and heated at 85° C. under reflux for 4 hours, thereby obtaining a crude reaction solution. Then, thereto was added dichloromethane as an internal standard, and GC analysis was conducted.

As a result of the analysis, the conversion of 1,1,1-trichloro-2-methyl-2-propanol was 99.0% and, on the basis of 1,1,1-trichloro-2-methyl-2-propanol, the yield of methyl 2-chloro-2-methylpropanoate was 55.6%, the yield of 1,1,3-trichloro-2-methylpropene was 17.5% and the yield of (1,1,1-trichloro-2-methyl) 2-chloro-2-methylpropanoate was 6.4%.

Example 11

A 1,2-dichloroethane solution containing 28 wt % of 1,1,1-trichloro-2-methyl-2-propanol was prepared by mixing 1,1,1-trichloro-2-methyl-2-propanol hemihydrate and 1,2-dichloroethane and drying by Molecular Sieves 4A. In a three necked flask an exit of which was connected to a Dimroth condenser the end of which was linked to an aqueous sodium hydroxide solution, 50.1 g of the solution (containing 14.0 g (0.079 mol) of 1,1,1-trichloro-2-methyl-2-propanol) and 16.0 g (0.164 mol) of sulfuric acid were mixed in a stream of nitrogen, and allowed to react for 1 hour. At the completion of the reaction, the liquid was separated into two layers, and 43.6 g of the upper layer and 16.3 g of the lower layer were collected. By NMR analyses, it was ascertained that the upper layer contained 36.1 g (0.365 mol) of 1,2-dichloroethane, 0.053 mol of 2-chloro-2-methylpropanoic acid chloride and 0.005 mol of 2-chloro-2-methylpropanoic sulfuric anhydride, and the lower layer contained 0.010 mol of 2-chloro-2-methylpropanoic sulfuric anhydride. In addition, by titration with the aqueous sodium hydroxide solution, it was ascertained that acidic gases were generated in an amount equivalent to 0.078 mol. This amount is 2.8 g in terms of hydrogen chloride, and corresponds to a 99% yield on the bases of the starting material alcohol used.

Example 12

The same reactor as used in Example 11 was used, and therein 2.8 g (0.087 mol) of methanol was added to the solution obtained as the upper layer in Example 11 and allowed to react at room temperature over 4 hours. By an NMR analysis of the solution obtained, it was found out that 0.060 mol of methyl 2-chloro-2-methylpropanoate was produced. This amount corresponds to a 76% yield on the basis of the starting material alcohol used for the reaction in Example 11. In addition, by titration with an aqueous sodium hydroxide solution, it was ascertained that acidic gases were generated in an amount equivalent to 0.049 mol. This amount is 1.8 g in terms of hydrogen chloride, and corresponds to a 62% yield on the bases of the starting material alcohol used in Example 11.

Example 13

Into a three necked flask equipped with a cold trap to an exit of the reactor was charged 17.3 g of sulfuric acid, and the pressure was reduced to 20 mmHg by means of a diaphragm pump. In addition, the exit of the diaphragm pump was linked to an aqueous sodium hydroxide solution.

While the internal temperature of the reactor was kept at 50° C., thereto was added a 52.2 wt % n-octane solution of the starting material alcohol at a rate of 0.94 g per minute, and at the same time the distillate was collected with the cold trap. By continuous addition over 520 minutes, 486.8 g in total of the starting material solution was added, and 365.6 g of the distillate was obtained. By an NMR analysis of the solution obtained, it was ascertained that 837.5 mmol of 2-chloro-2-methylpropanoic acid chloride was produced. This amount corresponds to a 58.8% yield on the basis of the starting material alcohol used.

In addition, by titration with the aqueous sodium hydroxide solution, it was ascertained that acidic gases were generated in an amount equivalent to 1.18 mol. This amount is 43.0 g in terms of hydrogen chloride, and corresponds to an 82% yield on the basis of the starting material alcohol used.

Example 14

An Inconel tube having an internal diameter of 4.35 mm was heated up to 520° C. by means of an electric furnace having an entire length of 30 cm. Into this were made to flow nitrogen (516 mL/hr) and methyl 2-chloro-2-methylpropanoate (2.65 g/hr) simultaneously for 4 hours. The product was collected in a dry ice trap. Specifically, 10.6 g (77.7 mmol) of methyl 2-chloro-2-methylpropanoate was charged thereinto, and 9.05 g of liquid was collected in the dry ice trap.

By an NMR analysis, it was found out that this liquid contained 5.15 g (51.4 mmol) of methyl methacrylate and 2.91 g (21.3 mmol) of methyl 2-chloro-2-methylpropanoate. The conversion of methyl 2-chloro-2-methylpropionate was 73%, and the selectivity for methyl methacrylate was 91%.

As shown in Examples 2 to 5 and 7 to 13, it has become able to obtain the intended compounds by using a catalyst in an amount of 0.03 to 1 mol with respect to 1 mol of the starting material alcohol. Further, it has become able to obtain chlorine of the starting material alcohol in the form of hydrogen chloride. Incidentally, it goes without saying that, though zinc chloride, sulfuric acid or activated clay was used as the catalyst in each of Examples, the same reactions can be conducted by the use of other Brønsted acids or Lewis acids.

Example 15

Synthesis example of
1H,1H,2H,2H-tridecafluorooctyl
2-chloro-2-methylpropanoate (15-1)

Into a 0.3-1 three necked flask were charged 40 g (0.215 mol) of 1,1,1-trichloro-2-methyl-2-propanol hemihydrate and 120 g (1.213 mol) of 1,2-dichloroethane. A distillation column was attached thereto, an azeotropic mixture of 1,2-dichloroethane and water was distilled away, and the rest was further concentrated to obtain a solution. The solution was added dropwise to a 0.5-1 three neck flask equipped with a reflux condenser and containing 44.19 g (0.454 mol) of sulfuric acid over 70 minutes while the inside temperature was kept at 35° C. or lower. After the completion of dropwise addition, intense generation of hydrochloric acid gas was confirmed. The stirring was carried out all night as it stood.

Thereto was further added 156.2 g (0.429 mol) of 1H,1H, 2H,2H-tridecafluoro-1-octanol over 30 minutes, heated up to 60° C., and stirred for 6 hours.

The reflux condenser was replaced with a distillation column, the pressure of the system was reduced to 15 mmHg and fractions having boiling points up to 90° C. were distilled away, to thereby obtain 85.3 g of a crude solution. The crude solution was subjected to a simple distillation, whereby 33.4 g (0.067 mol, boiling point: 242° C., yield: 33.1%) of 1H,1H, 2H,2H-tridecafluorooctyl 2-chloro-2-methylpropanoate was obtained at a GC purity of 94.6%.

Example 16

Synthesis example of
1H,1H,2H,2H-tridecafluorooctyl
2-chloro-2-methylpropanoate (15-1)

Into a 0.3-1 three necked flask were charged 40 g (0.215 mol) of 1,1,1-trichloro-2-methyl-2-propanol hemihydrate and 200 g (1.625 mol) of nitrobenzene. A distillation column was attached thereto, an azeotropic mixture of nitrobenzene and water was distilled away. To the solution was added 3.42 g (0.021 mol, 0.1 mol with respect to the raw alcohol) of iron chloride, followed by stirring.

Thereto was further added 156.2 g (0.429 mol) of 1H,1H, 2H,2H-tridecafluoro-1-octanol over 25 minutes, heated up to 120° C., and stirred for 7 hours. Then, it was fond out by gas chromatography analysis that the conversion of the 1,1,1-trichloro-2-methyl-2-propanoate was 83.8% and the yield of 1H,1H,2H,2H-tridecafluorooctyl 2-chloro-2-methylpropanoate (15-1) was 62.52%.

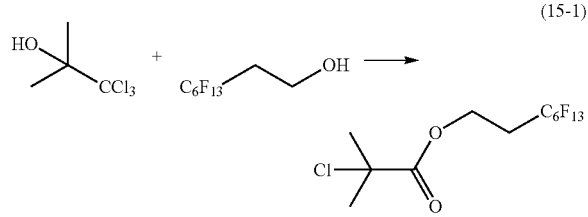

The structure of compound (15-1) as the product was assigned by $^1$H-NMR and $^{19}$F-NMR. The results thereof are shown below.

1H-NMR (300.4 MHz, CDCl$_3$, TMS) δ; 1.79(s,6H), δ; 2.45-2.62 (m,2H), δ; 4.49 (t, J=6.4 Hz, 2H)

$^{19}$F-NMR (300.4 MHz, CDCl$_3$) δ; −81.3 (s, 3F), δ; −114.0 (s, 2F), δ; −122.3 (s, 2F), δ; −123.3 (s, 2F)

Example 17

Synthesis example of 1H,1H,2H,2H-tridecafluorooctyl methacrylate (15-2)

An Inconel tube having an internal diameter of 4.35 mm was heated up to 540° C. by means of an electric furnace having an entire length of 30 cm. Into this were made to flow nitrogen (1.26 L/hr) and 1H,1H,2H,2H-tridecafluorooctyl 2-chloro-2-methylpropanoate (24.5 g/hr) simultaneously for 33 minutes. The product was collected in a dry ice trap.

Specifically, 13.6 g (29.0 mmol) of 1H,1H,2H,2H-tridecafluorooctyl 2-chloro-2-methylpropanoate was charged thereinto, and 12.4 g of liquid was collected in the dry ice trap. By an NMR analysis, it was found out that this liquid contained 1.36 g (3.09 mmol) of 1H,1H,2H,2H-tridecafluorooctyl methacrylate and 2.61 g (5.56 mmol) of 1H,1H,2H,2H-tridecafluorooctyl 2-chloro-2-methylpropanoate. The conversion of 1H,1H,2H,2H-tridecafluorooctyl 2-chloro-2-methylpropanoate was 81%, and the selectivity for 1H,1H,2H,2H-tridecafluorooctyl methacrylate (15-2) was 13%.

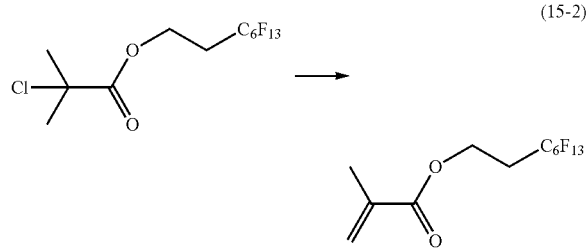

While the present invention has been described in detail and referring to specific embodiments, it is apparent for those skilled in the art that various modifications or changes can be made without departing from the spirit and scope of the present invention.

The present application is based on Japanese Patent Application No. 2012-193801 filed on Sep. 4, 2012, and the contents thereof are incorporated herein by reference.

The invention claimed is:

1. A method for producing an unsaturated acid and/or an unsaturated acid ester, comprising a process A of reacting a compound (1) represented by the following formula (1) at a temperature of 0° C. to 350° C. in the presence of a Brønsted acid catalyst and/or a Lewis acid catalyst, to prepare a compound (2) represented by the following formula (2);

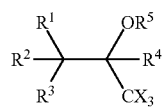

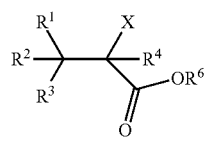

(wherein each of R$^1$, R$^2$ and R$^4$ independently represents a hydrogen atom, a deuterium atom or an alkyl group which has carbon number of 1 to 3 and may be substituted with a halogen atom and/or a deuterium atom; each of R$^3$ and R$^5$ independently represents a hydrogen atom or a deuterium atom; R$^6$ represents a hydrogen atom, a deuterium atom, or an alkyl group or an aryl group which has carbon number of 1 to 8 and may be substituted with a halogen atom and/or a deuterium atom; and X represents a chlorine atom, a fluorine atom, a bromine atom, or an iodine atom).

2. The production method according to claim 1, wherein the Brønsted acid catalyst and/or the Lewis acid catalyst is a compound represented by the following general formula (A) or mixture thereof;

$$M_n Y_m \quad (A)$$

(wherein M represents a hydrogen ion or a cation of metal or metalloid selected from the group consisting of the group 2 elements and the group 4-14 elements in the periodic table; Y represents an anion selected from the group consisting of halide ions, a sulfate ion, a nitrate ion, a carbonate ion, a hydrogencarbonate ion, a sulfide ion, an oxide ion, a hydroxide ion, a alkoxide ions, a phosphate ion, an acetate ion, and a perchlorate ion; and n and m are numbers satisfying the expression, cation M's valence×n=anion Y's valence×m).

3. The production method according to claim 2, wherein M is a cation of metal selected from the group consisting of zinc, iron and copper, and Y is a fluoride ion, a chloride ion or a bromide ion.

4. The production method according to claim 1, wherein the Lewis acid catalyst is an activated clay, an acid clay, a zeolite, a heteropoly acid, or an ion exchange resin.

5. The production method according to claim 1, wherein the Brønsted acid catalyst and/or the Lewis acid catalyst is present in a ratio of 0.001 to 1 mol with respect to 1 mol of the compound (1).

6. The production method according to claim 1, wherein the process A contains a step of adding an alcohol which has carbon number of 1 to 8 and may be substituted with a halogen atom and/or a deuterium atom, exclusive of the compound (1) represented by formula (1), and/or water.

7. The production method according to claim 1, further comprising, subsequent to the process A, a process B of preparing a compound (3) represented by the following formula (3) from the product of the process A containing the compound (2);

[Chem. 3]

(3)

(wherein $R^1$, $R^2$, $R^4$ and $R^6$ have the same meanings as above, respectively).

8. The production method according to claim 1, wherein each of $R^1$, $R^2$, $R^4$ and $R^6$ is independently a hydrogen atom, a deuterium atom, or an alkyl group which has carbon number of 1 to 3 and may be substituted with a deuterium atom.

9. The production method according to claim 8, wherein each of $R^1$ and $R^2$ is independently a hydrogen atom or a deuterium atom, and each of $R^4$ and $R^6$ is a methyl group which may be substituted with a deuterium atom.

10. The production method according to claim 9, further comprising, prior to the process A, a process C of reacting an acetone which may be substituted with a deuterium atom, with a halogenoform or a deuterated halogenoform, to prepare the compound (1).

* * * * *